United States Patent [19]

Konrad et al.

[11] 4,452,603

[45] Jun. 5, 1984

[54] PROCESS FOR DYEING HAIR AND COMPOSITION THEREFOR

[75] Inventors: Eügen Konrad; Hans Husemeyer, both of Darmstadt; Herbert Mager, Freibourg, all of Fed. Rep. of Germany

[73] Assignee: Wella Aktiengesellschaft, Darmstadt, Fed. Rep. of Germany

[21] Appl. No.: 205,321

[22] PCT Filed: Dec. 17, 1979

[86] PCT No.: PCT/EP79/00099

§ 371 Date: Jul. 17, 1980

§ 102(e) Date: Jul. 17, 1980

[87] PCT Pub. No.: WO80/01241

PCT Pub. Date: Jun. 26, 1980

[51] Int. Cl.$^3$ ............................................. D06P 3/04
[52] U.S. Cl. .................................... 8/405; 8/406; 8/407; 8/408; 8/409; 8/410; 8/411; 8/412
[58] Field of Search ........................ 8/405, 406, 411

[56] References Cited

U.S. PATENT DOCUMENTS

| | | | |
|---|---|---|---|
| 3,988,110 | 10/1976 | Zviak et al. | 8/406 |
| 4,010,200 | 3/1977 | Kalonissis et al. | 8/406 |
| 4,125,367 | 11/1978 | Bugaut et al. | 8/411 |
| 4,268,264 | 5/1981 | Grollier et al. | 8/406 |

FOREIGN PATENT DOCUMENTS

| | | | |
|---|---|---|---|
| 1619613 | 9/1972 | Fed. Rep. of Germany | 8/406 |
| 50-5539 | 1/1975 | Japan | 8/411 |

OTHER PUBLICATIONS

Abstract, vol. 652, pp. 289–290, O.G. 11/6/1951.

*Primary Examiner*—Dale R. Ore
*Attorney, Agent, or Firm*—Michael J. Striker

[57] ABSTRACT

The object of the invention is a composition and a process for the oxidative dyeing of hair on the basis of a 1-(3-hydroxyalkyl)-2,4-diaminobenzene as coupler substance.

11 Claims, No Drawings

PROCESS FOR DYEING HAIR AND COMPOSITION THEREFOR

SUMMARY

At least one 1-($\beta$-hydroxyalkyl)-2,4-diaminobenzene of the general formula

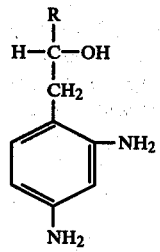

wherein R signifies a hydrogen atom, a $CH_3$ or $C_2H_5$ group, is used as coupler substance, also in the form of its inorganic or organic salts, for the oxidative dyeing of hair.

The coupler substance is used in a concentration of approximately 0.01 to 4.0 percent by weight, i.e. as a mixture with the usual developer substances and, in given instances also coupler substances. When mixed with 1,4-diaminobenzene and derivatives of 1,4-diaminobenzenes as developer substances, the aforenoted 1-($\beta$-hydroxyalkyl)-2,4-diaminobenzenes will produce relatively cold, highly intensive blue hues without a reddish proportion. Production may furthermore be made of ashen natural hues and of dark natural hues, particularly of a blue-black.

The object of the invention is a composition and a process for the oxidative dyeing of hair on the basis of a 1-($\beta$-hydroxyalkyl)-2,4-diaminobenzene as coupler substance.

Dyeing compositions on the basis of oxidative dyes have obtained essential importance in the dyeing of hair. The coloration results herein by a reaction of certain developer substances with certain coupler substances in the presence of a suitable oxidant.

It is, above all, 2,5-diaminotoluene, 1,4-diaminobenzene, p-aminophenol, and 3-methyl-4-aminophenol which are being used as developer substances. Preferably used coupler substances are $\alpha$-naphtol, resorcin, 4-chlororesorcin, m-aminophenol and derivatives of m-phenylene diamine such as m-toluylene diamine and 2,4-diaminoanisole. These derivatives, and also the m-phenylene diamine itself have obtained significance herein as so-called blue couplers due to their capacity of generating blue tints during oxidative coupling with 1,4-diaminobenzene or, respectively, derivatives of 1,4-diaminobenzene.

Oxidative dyes used for the dyeing of human hair must satisfy numerous special demands. They must be unobjectionable as to toxicology and dermatology and allow dyeing to the desired intensity.

It is furthermore required that a combination of suitable developer and coupler substances will enable the production of a wide range of differing color nuances. Furthermore, the resulting coloring should, to a good degree, be fast to light and resistant to permanent wave treatment, acids, and rubbing. Such hair coloring must, at any rate, remain stable against the influence of light, rubbing, and chemical agents, for a period of at least 4 to 6 weeks.

The aforenoted requirements cannot yet fully be satisfied by the m-phenylenediamine presently used as blue coupler in hair dyeing compositions, nor by its derivatives m-toluylenediamine and 2,4-diaminoanisole and also not by recently recommended blue couplers, such as, for instance, 1-hydroxy-3-amino-6-chlorobenzene and 2,4-diaminophenoxyethanol.

In respect of the above, it was found that compositions for the oxidative dyeing of hair, containing as coupler substance a minimum of one 1-($\beta$-hydroxyalkyl)-2,4-diaminobenzene of the general formula:

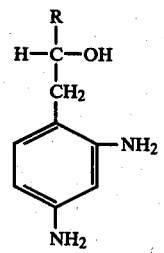

wherein R may signify a hydrogen atom, a $CH_3$ or a $CH_2H_5$ group, will satisfy to a particular high degree the demands as set, this also when in the form of its organic or inorganic salts.

The 1-($\beta$-hydroxyalkyl)-2,4-diaminobenzenes contained as coupler substances in the hair dye compositions as per invention, are well soluble in water, wherein solubility may even be enhanced by the addition of alkalis, such as, for instance, sodium hydroxide, and they have also an excellent storability particularly as component of the hair dyeing compositions as per invention.

The aforenamed coupler substances of which the 1-($\beta$-hydroxyalkyl)-2,4 diaminobenzene is preferred, should be contained in the hair dyeing compositions in a concentration of approximately 0.01 to 4.0 percent by weight, preferably 0.02 to 2.0 percent by weight.

The hair dyeing substances may, furthermore, additionally contain known coupler substances, particularly $\alpha$-naphthol, 3,4-diaminobenzoic acid, resorcin, 4-chlororesorcin, m-aminophenol and 3-amino-6-methylphenol. 4-oxy-1,2-methylene dioxybenzene may advantageously be used as coupler.

Of the known developer substances, it is above all, 1,4-diaminobenzene, p-aminophenol and 3-methyl-4-aminophenol that come into consideration as components of hair dyeing compositions as per invention. 2,5-diaminobenzyl alcohol may, furthermore, also be used as suitable developer.

1-($\beta$-hydroxyalkyl)-2,4-diaminobenzenes used as per invention, as well as the known coupler and developer substances may be contained in these hair dyeing compositions, either separately by themselves or as mixtures thereof.

The total quantity of the developer substance-coupler substance combination contained in the hair dyeing compositions described herein, should amount to approximately 0.1 to 5.0 percent by weight, preferably 0.5 to 3.0 percent by weight.

The developer substances are generally used in approximately equimolar quantities relative to the coupler substances. It will, however, not be of disadvantage if the developer component is contained herein in a certain excess of deficiency pertaining to the aforenoted relation.

The hair dyeing compositions of the present application may, furthermore, contain other coloring components such as, f.i., 6-amino-3-methylphenol, as well as customary direct-drawing dyes, for instance triphenylmethane dyes such as Diamond Fuchsin (C.I. 42 510) and Leather Ruby HF (C.I. 42 520), aromatic nitro dyes such as 2-nitro-1,4-diaminobenzene and 2-amino-4-nitrophenoll, azo dyes such as Acid Brown 4 (C.I. 14 805) and Acid Blue 135 (C.I. 13 385), anthraquinone dyes such as Disperse Red 15 (C.I. 60 710) and Disperse Violet 1, (C.I. 60 710) and Disperse Violet 1 (C.I. 61 100), and also 1,4,5,8-tetraamino-anthraquinone and 1,4-diamino-anthraquinone.

Furthermore, the hair dyeing compositions may contain other customary cosmetic additives, for instance antioxidants such as ascorbic acid or sodium sulfite, perfume oils, complex formers, wetting agents, emulgators, thickeners, hair care ingredients and others.

The form of preparation may be as solution, preferably as cream, as gel or as emulsion. Its constitution represents a mixture of the dye components with ingredients customary for such preparations. As for the customary ingredients of creams, emulsions or gels, mention may be made for instance of wetting agents or emulgators from the classes of anionic, cationic or non-ionogenic surfactants such as fatty alcohol sulfates, alkyl sulfonates, alkylbenzene sulfonates, alkyltrimethyl ammonia salts, ethoxylated fatty alcohols, ethoxylated nonylphenols, fatty acid alkanol amides, furthermore thickeners such as higher fatty alcohols, starch, cellulose derivatives, paraffin oil and fatty acids and also hair care ingredients such as lanolin derivatives, cholesterol and pantothenic acid. The aforenoted ingredients are used in quantities customary for such purposes, f.i. wetting agents and emulgators in concentrations of approximately 0.5 to 30 percent by weight, whilst thickeners may be contained in the preparations in quantities of approximately 0.1 to 25 percent by weight.

Depending upon their constitution, the dyeing compositions as per invention may react slightly acidic, neutral, or alkaline. Particularly in the alkaline range they will be of a pH value between 8.0 and 11.5, adjustment being preferably made with ammonia. Use may however also be made of organic amines f.i. monoethanolamine or triethanolamine.

In the process for oxidative dyeing of hair, as per invention, the hair dyeing compositions, containing a combination of developer substances known in hair dyeing, with at least one 1-($\beta$-hydroxyalkyl)-2,4-diaminobenzene of the aforenoted formula as coupler substance and, in the respective instance also containing known coupler substances, are mixed shortly before use with an oxidant and the mixture is applied onto the hair. As oxidants for developing the hair coloring, it is mainly hydrogen peroxide that comes into consideration, for instance as 6% aqueous solution or, respectively, as its adductive compounds with urea, melamin or sodium borate. The mixture is allowed to act upon the hair for 10 to 45 minutes, preferably 30 minutes, at 15° to 50° C., the hair then being rinsed with water and dried thereupon. In given instances, washing with a shampoo is made after this rinsing, and a second rinse may possibly be made using a weak organic acid such as, f.i. citric acid or tartaric acid.

Various ways of synthesis are known from literature for the production of a 1-($\beta$-hydroxyalkyl)-2,4-diaminobenzenes contained in the hair dyeing compounds described afore. Production of 1-($\beta$-hydroxyethyl)-2,4-diaminobenzene may, for instance, proceed from $\beta$-phenylethyl alcohol. For the protection of the OH group, the $\beta$-phenylethyl alcohol is acetylized first and nitrated thereafter. Catalytic hydration of the resulting 2,4-dinitro compound and subsequent deactylization will give a high yield of 1-($\beta$-hydroxyethyl)-2,4-diaminobenzene.

Regarding the possibilities in respect of coloration, the hair dyeing composition as per invention will, depending upon the type and constitution of the color components, offer a wide range of various color nuances, ranging from blond tones over brown, ashen, violet hues up to blue and black color tints. The color tints obtained are distinguished by the strong intensity of their coloring.

Use of 1-($\beta$-hydroxyalkyl)-2,4-diaminobenzenes of the aforenoted formula is of particular importance in the hair dyeing compositions described herein since it constitutes an advance in respect of toxicology and dermotology f.i. when compared to the known blue coupler 2,4-diaminotoluene, 2,4-diaminoanisole and 1,3-diaminobenzene, such advance being based upon the hydroalkyl group bonded to the substituted benzene nucleus and the reduction of lipoid solubility resulting therefrom.

The aforenoted 1-($\beta$-hydroxyalkyl)-2,4-diaminobenzenes when combined as coupler substances with 1,4-diaminobenzene and derivatives of 1,4-diaminobenzene will yield relatively cold highly intensive blue tints without a reddish portion, which cannot be obtained without coupler substances, such as, for instance, 2,4-diaminotoluene, 2,4-diaminoanisole, 2,4-diaminophenoxyethanol as usually employed in hair dyeing compositions.

If the blue coupler which is absolutely required for obtaining ashen tints when used with 1,4-diamino compounds noted afore as developer substances, yields bluish tints with a red or violet hue, this will make it impossible or very difficult to obtain ashen hues. Contrary to the aforegoing, the advantageous characteristic of 1-($\beta$-hydroxyalkyl)-2,4-diaminobenzene as per invention will allow to produce bluish hues without the reddish component, so that it is possible without any problems to dye the hair in ashen natural hues.

The superior coloring characteristics of the hair dyeing compositions as per the present application are furthermore manifested in the fact that the 1-($\beta$-hydroxyalkyl)-2,4-diaminobenzenes contained as coupler substances will allow the production also of dark natural hues particularly blue-block.

Finally, it will also be possible by using these hair dyeing compositions to color greyed hair that has not suffered previous chemical damage, with no problems and with a covering power not obtained hitherto.

The object of the invention will be explained more closely in the following embodiments:

| Embodiments | |
|---|---|
| Embodiment 1 | Hair dyeing composition as gel |
| 0,5 g | 1-($\beta$-hydroxyethyl-2,4-diaminobenzene-dihydrochloride |
| 0,5 g | 2,5-diaminotoluenesulfate |
| 0,3 g | ascorbic acid |
| 1,0 g | hydroxyethyl cellulose, high viscosity |
| 5,0 g | diglycolether sulfate of lauryl alcohol, sodium salt (28% aqueous solution) |

-continued

| Embodiments | |
|---|---|
| Embodiment 1 | Hair dyeing composition as gel |
| 10,0 g | ammonia, 22% |
| 82,7 g | water |
| 100,0 g | |

50 g of the hair dyeing composition are mixed with 50 mL hydrogen peroxide solution (6%) shortly before using, and the mixture is allowed to act upon blond human hair for 30 minutes at 40° C. Rinsing with water and drying are then made. The hair has obtained an intensive blue coloring.

| Embodiment 2 | Hair dyeing composition as gel |
|---|---|
| 0,5 g | 1-(β-hydroxyethyl)-2,4-diaminobenzene-dihydrochloride |
| 1,0 g | 1,4-diaminobenzene |
| 0,5 g | resorcin |
| 0,2 g | m-aminophenol |
| 0,3 g | ascorbic acid |
| 15,0 g | oleic acid |
| 7,0 g | isopropanol |
| 10,0 g | ammonia, 22% |
| 65,5 g | water |
| 100,0 g | |

50 g of this hair dyeing composition are mixed with 50 mL hydrogen peroxide solution (6%) shortly before using and the mixture is then applied onto blond human hair. After an application period of 30 minutes at 40° C. rinsing with water and drying are made. The hair has been dyed to a deep blue-black tint.

| Embodiment 3 | Hair dyeing composition as creme |
|---|---|
| 0,5 g | 1-(β-hydroxyethyl)-2,4-diaminobenzene-dihydrochloride |
| 0,3 g | p-aminophenol |
| 0,3 g | sodium sulfite, anhydrous |
| 15,0 g | cetyl alcohol |
| 3,5 g | diglycolether sulfate of lauryl alcohol, sodium salt (28% aqueous solution) |
| 3,0 g | ammonia, 22% |
| 77,4 g | water |
| 100,0 g | |

50 g of this hair dyeing composition are mixed with 50 mL hydrogen peroxide (6%) shortly before use and the mixture is then applied onto blond human hair. After an application time of 30 minutes at 40° C. rinsing with water and drying are made. The hair has obtained a rose coloring.

All percentages quoted in the present application are percent by weight.

We claim:

1. Composition for the oxidative dyeing of hair, characterized by containing 0.1 to 5.0 percent by weight of a combination of a developer substance and a coupler substance, also in the form of its inorganic or organic salts, said coupler substance being a 1-(β-hydroxyalkyl)-2,4-diaminobenzene of the general formula

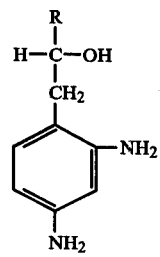

wherein R signifies a hydrogen atom, or a CH$_3$ or a C$_2$H$_5$ group.

2. Composition as per claim 1, characterized by containing as coupler substance, also in the form of its inorganic or organic salts, 1-(β-hydroxyethyl)-2,4-diaminobenzene.

3. Composition as per claim 1, characterized by containing the coupler substances as per invention in a concentration of approximately 0.01 to 4.0 percent by weight.

4. Composition as per claim 1, characterized by containing at least one of the following developer substances: 1,4-diaminobenzene, 2,5-diaminotoluene, 2,5-diaminobenzylalcohol, p-aminophenol, and 3-methyl-4-aminophenol.

5. Composition as per claim 1, characterized by containing at least one of the following as further coupler substances: α-naphtol, 3,4-diaminobenzoic acid, resorcin, 4-chlororesorcin, m-aminophenol, 4-oxy-1,2-methylenedioxybenzene and 3-amino-6-methylphenol.

6. Composition as per claim 1, characterized by additionally containing 6-amino-3-methylphenol as color component.

7. Composition as per claim 1, characterized by containing at least one of the following direct-drawing dyes: Diamond Fuchsion (C.I. 42 510), Leather Ruby HF (C.I. 42 520), 2-nitro-1,4-diaminobenzene, 2-amino-4-nitrophenol, Acid Brown 4 (C.I. 14 805), Acid Blue 135 (C.I. 13 385), Disperse Red 15 (C.I. 60 710), Disperse Violet 1 (C.I. 61 100), 1, 4, 5, 8-tetraminoanthraquinone and 1,4-diamino-anthraquinone.

8. Composition as per claim 1, characterized by additionally containing antioxidants.

9. Composition as per claim 1, characterized by additionally containing wetting agents, emulgators and/or thickeners.

10. Composition as per claim 8, wherein said antioxidant is selected from the group consisting of ascorbic acid and sodium sulfite.

11. Process for the oxidative dyeing of hair, characterized by applying onto the hair an effective amount for dyeing of a mixture of an oxidant, selected from the group consisting of hydrogen peroxide and its adductive compounds with urea, melamin and sodium borate, and a hair dyeing composition of claim 1; allowing said mixture to act on the hair for about 10 to 45 minutes at a temperature of 15° to 50° C.; and subsequently rinsing the hair.

* * * * *

UNITED STATES PATENT AND TRADEMARK OFFICE
CERTIFICATE OF CORRECTION

PATENT NO. : 4 452 603
DATED : June 5, 1984
INVENTOR(S) : Eügen Konrad; Hans Husemeyer. Herbert Mager It is certified that error appears in the above—identified patent and that said Letters Patent is hereby corrected as shown below:

On the title page, the following should be added.

-- (30) Foreign Application Priority Data
December 23, 1978 (DE) Fed.Rep.of Germany 28 55 917 --.

Signed and Sealed this

Eighth Day of January 1985

[SEAL]

Attest:

GERALD J. MOSSINGHOFF

*Attesting Officer*   *Commissioner of Patents and Trademarks*